(12) United States Patent
Desjardin et al.

(10) Patent No.: US 11,547,441 B2
(45) Date of Patent: Jan. 10, 2023

(54) RETENTION ANCHOR FOR SURGICAL ACCESS DEVICES

(71) Applicant: Covidien LP, Mansfield, MA (US)

(72) Inventors: Kevin Desjardin, Prospect, CT (US);
Astley C. Lobo, West Haven, CT (US);
Jacob C. Baril, Norwalk, CT (US);
Brian J. Creston, Madison, CT (US)

(73) Assignee: Covidien LP, Mansfield, MA (US)

( * ) Notice: Subject to any disclaimer, the term of this patent is extended or adjusted under 35 U.S.C. 154(b) by 341 days.

(21) Appl. No.: 16/795,809

(22) Filed: Feb. 20, 2020

(65) Prior Publication Data

US 2021/0259729 A1 Aug. 26, 2021

(51) Int. Cl.
*A61B 17/34* (2006.01)
*A61B 17/00* (2006.01)
(Continued)

(52) U.S. Cl.
CPC ...... *A61B 17/3423* (2013.01); *A61B 17/3421* (2013.01); *A61B 2017/00477* (2013.01);
(Continued)

(58) Field of Classification Search
CPC .... A61B 2017/3419; A61B 2017/3492; A61B 2017/3484; A61B 2017/3488;
(Continued)

(56) References Cited

U.S. PATENT DOCUMENTS

| 397,060 A | 1/1889 | Knapp |
|---|---|---|
| 512,456 A | 1/1894 | Sadikova |

(Continued)

FOREIGN PATENT DOCUMENTS

| DE | 202016107414 U1 | 1/2017 |
|---|---|---|
| EP | 0480653 A1 | 4/1992 |

(Continued)

OTHER PUBLICATIONS

Extended European Search Report issued in corresponding European Application No. 21158156.6 dated Jun. 29, 2021, 8 pages.

(Continued)

*Primary Examiner* — Marcela I. Shirsat
(74) *Attorney, Agent, or Firm* — Carter, DeLuca & Farrell LLP

(57) ABSTRACT

A surgical access assembly includes a cannula and a retention anchor including an annular body and a washer secured to the annular body. The annular body includes an inner side surface defining an opening therethrough, and the washer includes an inner terminal edge defining an opening therethrough that is aligned with the opening of the annular body. The elongated shaft of the cannula extends through the openings. The washer is transitionable between a first configuration in which the inner terminal edge of the washer is coincident with or disposed radially outwardly of the inner side surface of the annular body so that the retention anchor is slidable along the elongated shaft, and a second configuration in which the inner terminal edge of the washer extends radially inwardly of the inner side surface of the annular body and engages the elongated shaft to fix the retention anchor to the elongated shaft.

20 Claims, 4 Drawing Sheets

(51) Int. Cl.
  *F16B 39/24* (2006.01)
  *F16B 39/284* (2006.01)
  *A61M 25/02* (2006.01)
  *F16B 39/36* (2006.01)

(52) U.S. Cl.
  CPC .......... *A61B 2017/3419* (2013.01); *A61B 2017/3484* (2013.01); *A61B 2017/3492* (2013.01); *A61M 2025/024* (2013.01); *F16B 39/24* (2013.01); *F16B 39/284* (2013.01); *F16B 39/36* (2013.01)

(58) Field of Classification Search
  CPC ...... A61B 2017/00477; A61B 17/3462; A61B 17/3423; A61B 17/3421; A61M 25/02; A61M 2025/024; A61M 2025/0266; F16B 39/24; F16B 39/282; F16B 39/36; F16B 39/284
  USPC ....... 600/210, 201, 204, 217, 227–229, 231, 600/233, 235; 604/164.1, 164.11, 264, 604/27, 73, 93.01, 104, 117, 167.06, 174, 604/1, 78, 179
  See application file for complete search history.

(56) References Cited

U.S. PATENT DOCUMENTS

| | | | |
|---|---|---|---|
| 1,213,005 A | 1/1917 | Pillsbury | |
| 2,912,981 A | 11/1959 | Keough | |
| 2,936,760 A | 5/1960 | Gains | |
| 3,039,468 A | 6/1962 | Price | |
| 3,050,066 A | 8/1962 | Koehn | |
| 3,107,905 A * | 10/1963 | Lucas ................. | F16F 1/32 |
| | | | 248/200.1 |
| 3,253,594 A | 5/1966 | Matthews et al. | |
| 3,397,699 A | 8/1968 | Kohl | |
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A | 4/1990 | Haindl | |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,267,970 A | 12/1993 | Chin et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,496,142 A * | 3/1996 | Fodor ................... | F16B 43/004 |
| | | | 411/368 |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,520 A | 9/1997 | Bonutti | |

(56) References Cited

U.S. PATENT DOCUMENTS

| | | |
|---|---|---|
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,509,175 B2 * | 3/2009 | Sparks ............... A61N 1/0558 607/133 |
| 8,454,645 B2 | 6/2013 | Criscuolo et al. |
| 10,408,250 B2 * | 9/2019 | Webb ................ F16B 31/02 |
| 2008/0091146 A1 * | 4/2008 | Solovay ............. A61F 5/0036 604/174 |
| 2019/0290255 A1 * | 9/2019 | Pravongviengkham ................ B29D 23/00 |

FOREIGN PATENT DOCUMENTS

| | | |
|---|---|---|
| EP | 0610099 A2 | 8/1994 |
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

OTHER PUBLICATIONS

European Communication Pursuant to Article 94(3) EPC issued in corresponding to European Application No. 21 158 156.6 dated Jul. 22, 2022, 6 pages.

* cited by examiner

RETENTION ANCHOR FOR SURGICAL ACCESS DEVICES

FIELD

The present disclosure relates generally to surgical access devices. In particular, the present disclosure relates to a retention anchor for fixing a surgical access device in tissue.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor mechanism to prevent the cannula from backing out of the opening in the abdominal wall, for example, during manipulation of the laparoscopic instrument within the cannula or withdrawal of the laparoscopic instrument therefrom.

SUMMARY

This disclosure generally relates to a retention anchor for securing a surgical access device within tissue. The retention anchor provides a counter force during insertion and/or articulation of surgical instruments through the surgical access device. In aspects in which the surgical access device includes an anchor mechanism, the retention anchor is utilized in conjunction with the anchor mechanism to limit longitudinal movement of the surgical access device relative to the tissue (e.g., retropulsion and over-insertion) during, for example, receipt, manipulation, and/or withdrawal of surgical instruments therethrough.

The retention anchor includes an annular body and a washer affixed to the annular body that is movable relative thereto. This design increases the usability of the retention anchor by maximizing the fixation force on a surgical access device and minimizing the force required to move the retention anchor relative to the surgical access device, and makes manufacturing and assembly easier.

In one aspect, the disclosure provides a surgical access assembly including a cannula and a retention anchor. The cannula includes an elongated shaft, and the retention anchor includes an annular body and a washer secured to the annular body. The annular body includes an inner side surface defining an opening therethrough, and the washer includes an inner terminal edge defining an opening defined therethrough that is aligned with the opening of the annular body. The elongated shaft of the cannula extends through the openings of the annular body and the washer. The washer is transitionable between a first configuration in which the inner terminal edge of the washer is coincident with or disposed radially outwardly of the inner side surface of the annular body so that the retention anchor is slidable along the elongated shaft, and a second configuration in which the inner terminal edge of the washer extends radially inwardly of the inner side surface of the annular body and engages the elongated shaft to fix the retention anchor to the elongated shaft.

The inner side surface of the annular body may frictionally engage the elongated shaft of the cannula. The inner side surface of the annular body may include ridges.

The annular body may include a proximally-facing surface, and the washer may be positioned adjacent to the proximally-facing surface. The washer may include an outer terminal edge affixed to the annular body. The proximally-facing surface of the annular body may define an annular recess therein and, when the washer is in second configuration, the washer may be disposed within the annular recess.

In some aspects, when the washer is in the first configuration, the washer has a convex shape and when the washer is in the second configuration, the washer has a concave shape.

The washer may be more rigid than the annular body. The washer may be formed from a metal and the annular body may be formed from a rubber.

In another aspect, the disclosure provides a retention anchor for a surgical access device including an annular body and a washer secured to the annular body. The annular body includes an inner side surface defining an opening therethrough, and the washer includes an inner terminal edge defining an opening defined therethrough that is aligned with the opening of the annular body. The washer is transitionable between a first configuration in which the inner terminal edge of the washer is coincident with or disposed radially outwardly of the inner side surface of the annular body, and a second configuration in which the inner terminal edge of the washer extends radially inwardly of the inner side surface of the annular body.

The inner side surface of the annular body may include ridges.

The annular body may include a proximally-facing surface, and the washer may be positioned adjacent to the proximally-facing surface. The washer may include an outer terminal edge affixed to the annular body. The proximally-facing surface of the annular body may define an annular recess therein and, when the washer is in second configuration, the washer may be disposed within the annular recess.

In some aspects, when the washer is in the first configuration, the washer has a convex shape and when the washer is in the second configuration, the washer has a concave shape.

The washer may be more rigid than the annular body. The washer may be formed from a metal and the annular body may be formed from a rubber.

In yet another aspect, a method of securing a surgical access device to tissue includes: positioning an elongated shaft of a cannula within tissue; sliding a retention anchor disposed on the elongated shaft of the cannula distally until the retention anchor abuts an outer surface of the tissue, the retention anchor including an annular body having an inner surface defining an opening therethrough and a washer secured to the annular body and having an inner terminal edge defining an opening therethrough that is aligned with the opening of the annular body, the elongated shaft of the cannula extending through the openings of the annular body and the washer, the washer disposed in a first configuration in which an inner terminal edge of the washer is coincident with or disposed radially outwardly of an inner surface of the annular body so that the retention anchor is slidable along the elongated shaft; and moving the washer of the retention anchor to a second configuration in which the inner terminal edge of the washer extends radially inwardly of the inner side surface of the annular body and engages the elongated shaft to fix the retention anchor to the elongated shaft.

Moving the washer may include pressing the washer into an annular recess defined in the annular body of the retention anchor.

The method may further include expanding an expandable anchor of the cannula against an inner surface of the tissue.

The details of one or more aspects of the disclosure are set forth in the accompanying drawings and the description below. Other features, objects, and advantages of the aspects described in this disclosure will be apparent from the description and drawings, and from the claims.

DETAILED DESCRIPTION

Figure 1:
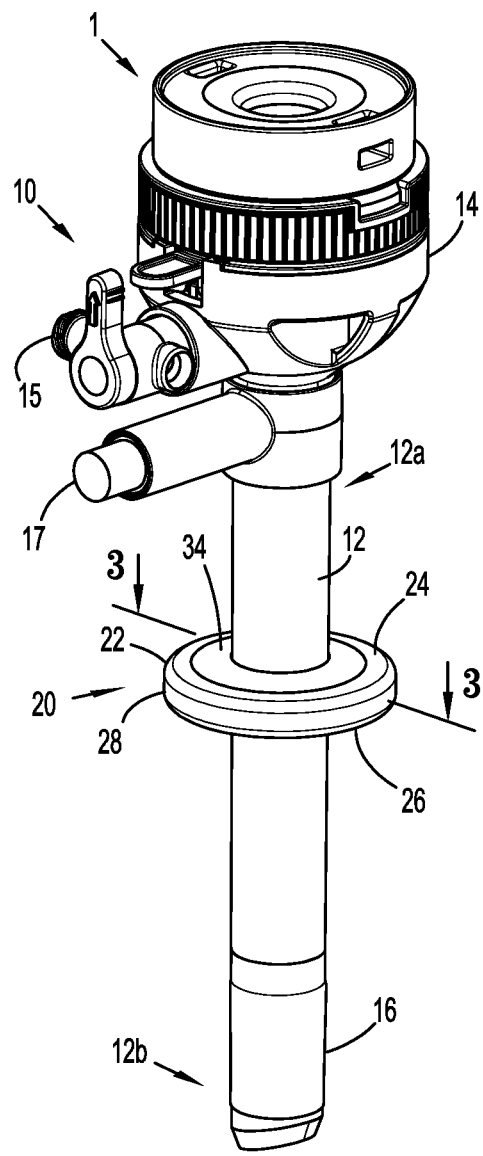
FIG. 1 is a perspective view of a surgical access assembly including a cannula and a retention anchor in accordance with an aspect of the disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Figure 5:
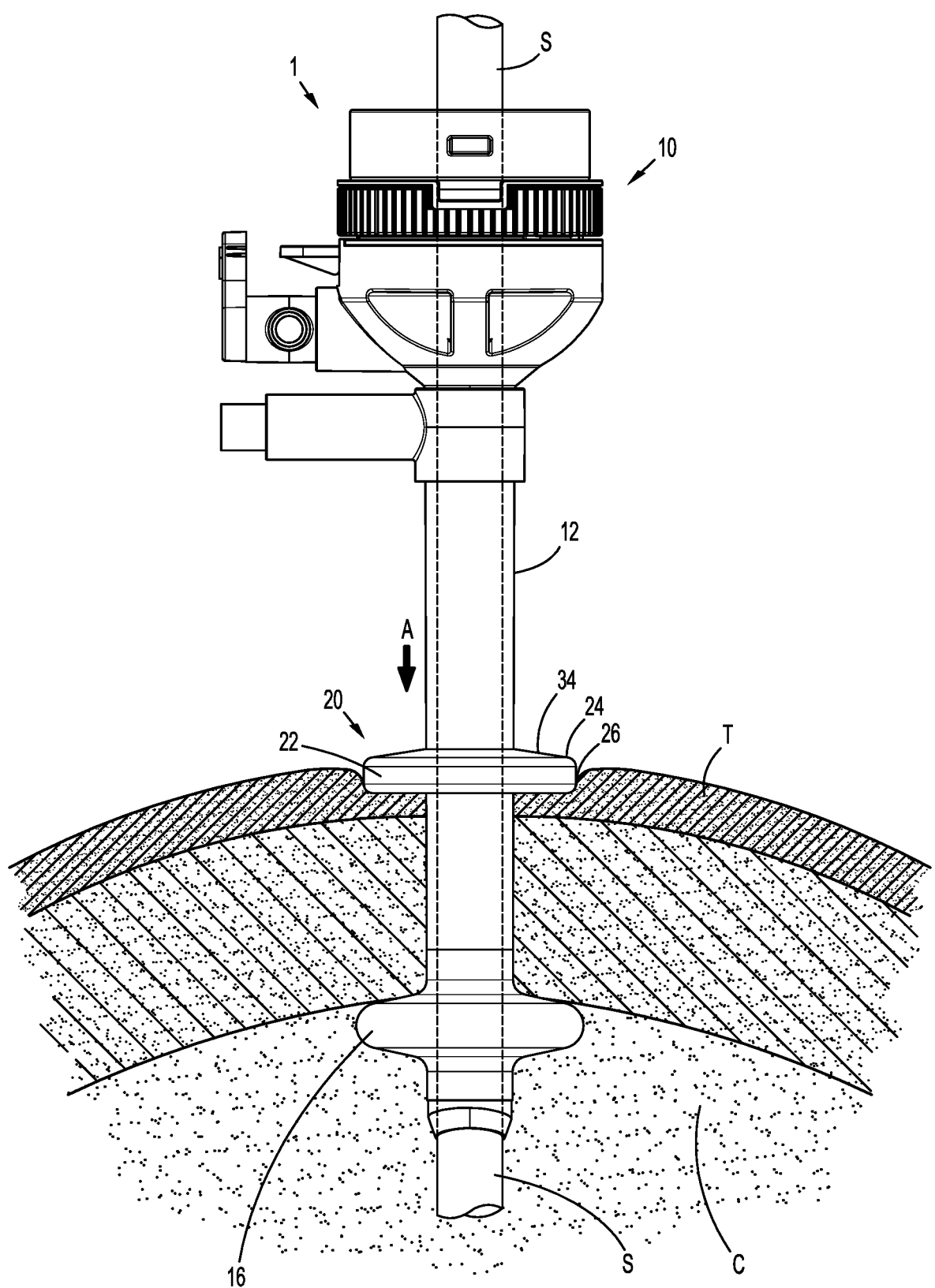
FIG. 5 is a side view of the surgical access assembly of FIG. 1, shown disposed within tissue.

FIG. 1 illustrates a surgical access system 1 including a surgical access device or cannula 10 and a retention anchor 20. The cannula 10 generally includes an elongated shaft 12 supporting an instrument housing 14 on a proximal or first end portion 12a thereof and an expandable anchor 16 (e.g., an inflatable anchor, such as a balloon, or a contractable anchor, such as a collapsible flange) on a distal or second end portion 12b thereof. The expandable anchor 16 secures the cannula 10 against an inner surface of a body wall, such as an abdominal wall, as seen in FIG. 5.

The retention anchor 20 is supported on the elongated shaft 12 of the cannula 10. The retention anchor 20 is releasably engageable with the elongated shaft 12, and slidable therealong to adjust the position of the retention anchor 20 on the elongated shaft 12. The retention anchor 20 secures the cannula 10 against an outer surface of the body wall and stabilizes the cannula 10 relative to the body wall.

Generally, the cannula 10 is employed during surgery (e.g., laparoscopic surgery) to access a surgical site and may, in various aspects, provide for the sealed insertion of surgical instruments into an insufflated body cavity, such as an abdominal cavity. The cannula 10 is usable with an obturator (not shown). The obturator generally includes an elongated body supporting a tip on a distal end thereof. The tip can have a bladed or non-bladed (e.g., blunt) penetrating distal end that can be used to incise or separate tissue of the body wall so that the cannula 10 can be introduced therethrough. The cannula 10 and the obturator may be capable of being selectively connected together. For example, the obturator may be inserted into and through the cannula 10 until a handle housing of the obturator engages, e.g., selectively locks into, the instrument housing 14 of the cannula 10. In this initial position, the cannula 10 and the obturator, which together form a trocar assembly, are employed to tunnel through a body wall, e.g., an abdominal wall, either by making a new passage through the body wall or by passing through an existing opening through the body wall. Once the trocar assembly has tunneled through the body wall, the obturator is removed, leaving the cannula 10 in place, e.g., in an incision created by the trocar assembly. The instrument housing 14 of the cannula 10 may include an insufflation port 15 that provides insufflation fluid (e.g., gases) into the body cavity, seals and/or valves (not shown) that allows surgical instrument to be inserted into the body cavity while preventing the escape of the insufflation fluid therefrom, and an anchor inflation port 17 which is in fluid communication with the expandable anchor 16 to expand and/or contract the expandable anchor 16.

For a detailed description of the structure and function of exemplary surgical access devices suitable for use with a retention anchor of the present disclosure, reference may be made to U.S. Pat. Nos: 7,691,089; 8,926,508; and 10,299,778, the entire contents of each of which are hereby incorporated by reference herein.

Figure 2:
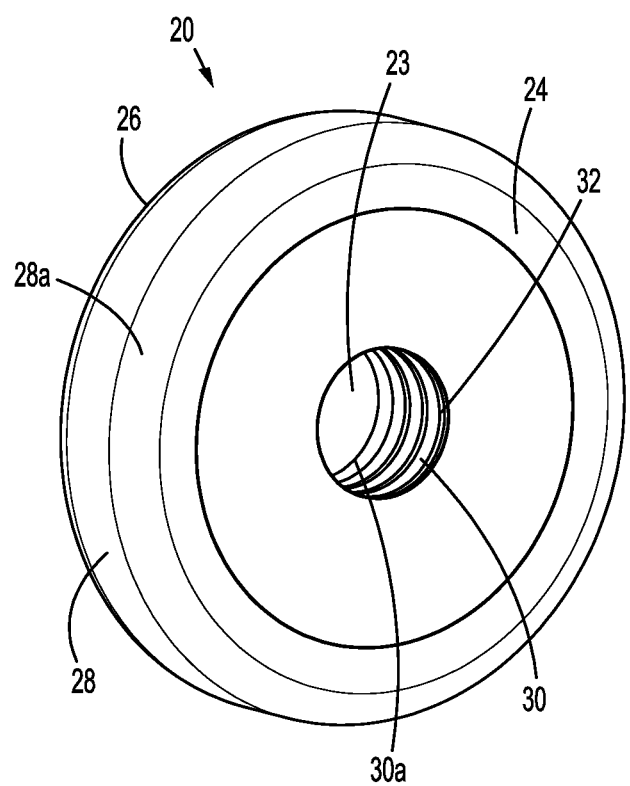
FIG. 2 is a perspective view of the retention anchor of the surgical access assembly of FIG. 1.

Turning now to FIG. 2, in conjunction with FIG. 1, the retention anchor 20 includes an annular body 22 having a first or proximally-facing surface 24, a second or distally-facing surface 26, an outer side surface 28, and an inner side surface 30. The outer and inner side surfaces 28, 30 extend between and interconnect the first and second surfaces 24, 26 and respectively define outer and inner terminal edges 28a, 30a of the retention anchor 20.

The inner side surface 30 defines an opening 23 through the annular body 22 that is sized and shaped to accommodate the elongated shaft 12 of the cannula 10 in a friction fit manner. The inner side surface 30 of the annular body 22 includes ridges 32 extending into the opening 23 to enhance the grip of the annular body 22 about the elongated shaft 12 of the cannula 10 and to limit movement of the retention anchor 20 relative to the cannula 10. It should be understood that in addition to or as an alternative to the ridges 32, the inner side surface 30 of the annular body 22 may include protrusions, bumps, projections, or other textured finishes to aid in retaining the retention anchor 20 on the elongated shaft 12 of the cannula 10 while allowing movement of the annular body 22 relative to the elongated shaft 12.

Figure 3:
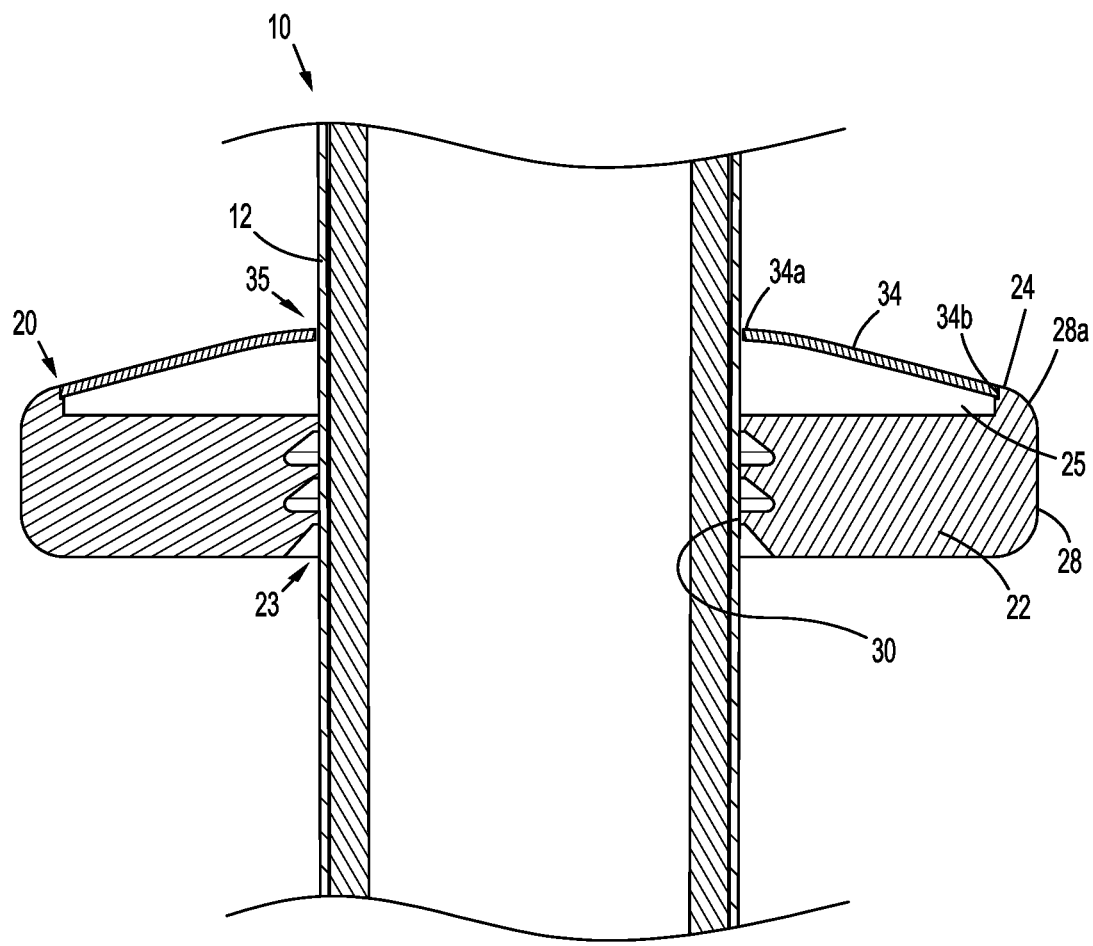
FIG. 3 is cross-sectional view of the surgical access assembly of FIG. 1, taken along section line 3-3 of FIG. 1, shown with the retention anchor in a first configuration.
Figure 4:
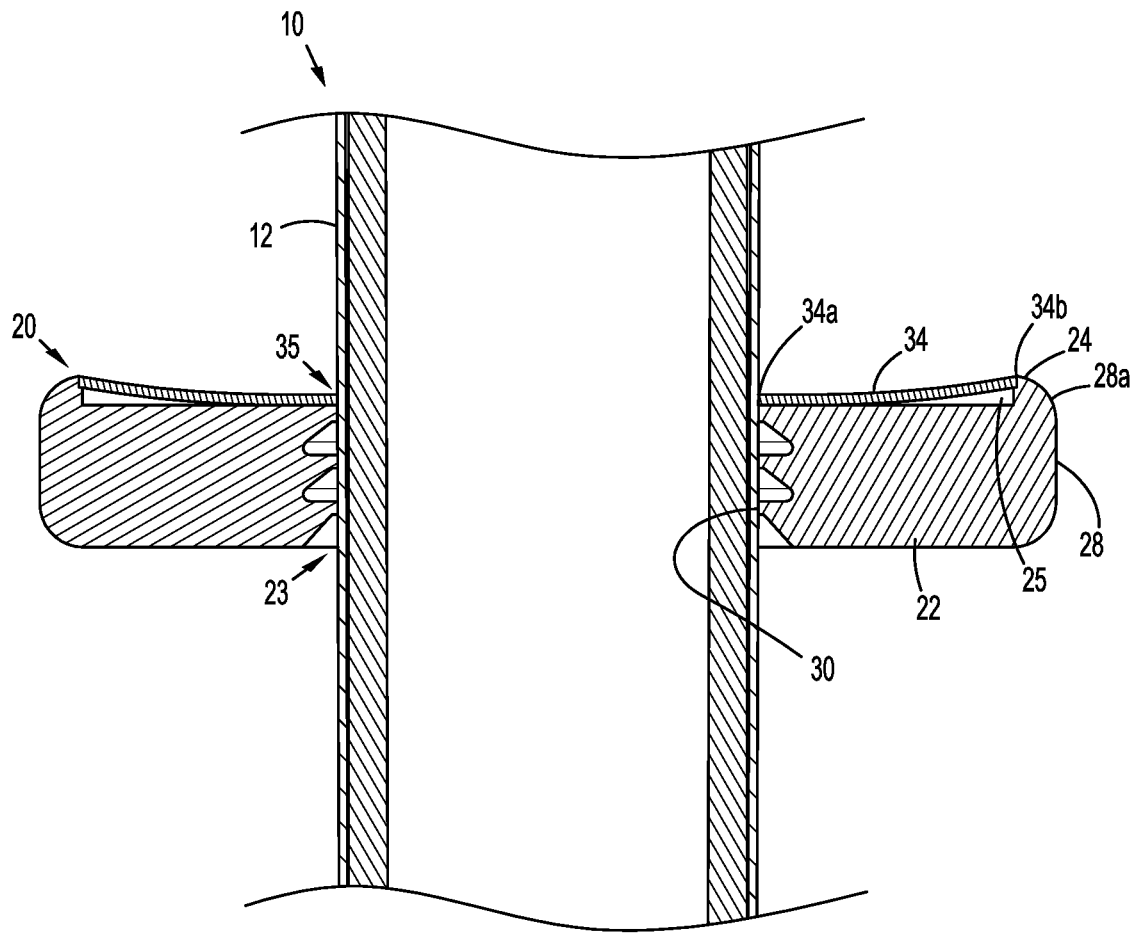
FIG. 4 is a cross-sectional view of the surgical access assembly of FIG. 3, shown with the retention anchor in a second configuration.

As shown in FIGS. 3 and 4, the annular body 22 includes an annular recess 25 defined in the first surface 24. The annular recess 25 extends from the inner side surface 30 of the annular body 22 radially outwardly towards the outer side surface 28, but is spaced inwardly of the outer terminal edge 28a such that the annular recess 25 extends across a majority of the first surface 24 (e.g., across more than about 50% of the surface area of the first surface 24 and, in some aspects, across more than 75% of the surface area of the first surface 24). The annular recess 25 is sized and shaped to retain a washer 34 therein.

The washer 34 is a thin, flat annular disk including an inner terminal edge 34a defining an opening 35 therethrough, and an outer terminal edge 34b. The opening 35 is aligned with the opening 23 defined through the annular body 22 to accommodate the elongated shaft 12 of the cannula 10 therethrough. The washer 34 is positioned adjacent to the first surface 24 of the annular body 22 and is transitionable between a first or clearance configuration having a convex shape, as seen in FIG. 3, and a second or interference configuration having a concave shape, as seen in FIG. 4.

The annular body 22 of the retention anchor 20 is formed from a flexible material, such as rubber, plastic, or other suitable polymer (e.g., elastomers). The washer 34 is formed from a material that is more rigid than the annular body 22, such as a metal (e.g., a thin sheet of metal). The washer 34 is affixed to the annular body 22 by over-molding or insert molding the annular body 22 to the washer 34 such that the outer terminal edge 34b of the washer 34 is retained within the annular body 22 to securely attach the washer 34 to the annular body 22. The washer 34 is affixed to the annular body 22 only at the outer terminal edge 34b such that the inner terminal edge 34a is movable relative to the annular body 22.

The washer 34 has an outwardly biased dome shape, as shown in FIG. 3, with the outer terminal edge 34b of the washer 34 disposed within the annular body 22 and the inner terminal edge 34a of the washer 34 extending upwardly away from the first surface 24 of the annular body 22. In this first configuration, the washer 34 has a convex shape, and the inner terminal edge 34a of the washer 34 is coincident with or disposed radially outwardly of the inner side surface 30 of the annular body 22 so that only the annular body 22 is engaged with the elongated shaft 12 of the cannula 10 and the retention anchor 20 is free to slide along the elongated shaft 12.

The washer 34 is transitionable to the second configuration, as shown in FIG. 4, by pressing the washer 34 towards the annular body 22. Since the outer terminal edge 34b of the washer 34 is affixed to the annular body 22, the inner terminal edge 34a of the washer 34 is moved downwardly into the annular recess 25 of the first surface 24 of the annular body 22. In this second configuration, the washer 34 has a concave shape, and the inner terminal edge 34a of the washer 34 extends radially inwardly of the inner side surface 30 of the annular body 22 and engages the elongated shaft 12 of the cannula 10 thereby fixing the retention anchor 20 to the elongated shaft 12 (e.g., locking the retention anchor 20 onto the cannula 10 by friction fit).

FIG. 5 illustrates the surgical access assembly 1 disposed within tissue "T," e.g., an abdominal wall. The retention anchor 20 is secured to the cannula 10 prior to introducing the cannula 10 into the tissue "T" (e.g., the retention anchor 20 may be pre-installed on the cannula 10 during manufacture or may be placed on the cannula 10 prior to use in the operating room). The elongated shaft 12 of the cannula 10 is received through the tissue "T" (e.g., by utilizing an obturator (not shown) to facilitate entry of the cannula 10 through the tissue "T"), and the expandable anchor 16 is inflated within a body cavity "C" to prevent the cannula 10 from being withdrawn through the tissue "T." The retention anchor 20, is disposed on the elongated body 12 of the cannula 10 in the first configuration (FIG. 3) and is slid distally along the elongated shaft 12 of the cannula 10 until the retention anchor 20 abuts or presses on the tissue "T."

The retention anchor 20 is then transitioned to the second configuration (FIG. 4) by pressing the washer 34 down into the annular recess 25 of the annular body 22 of the retention anchor 20, in the direction of arrow "A," to lock the retention anchor 20 onto the elongated shaft 12 of the cannula 10 by friction fit between the washer 34 and the elongated shaft 12. The tissue "T" is thus sandwiched between the expandable anchor 16 and the retention anchor 20 to prevent the cannula 10 from being withdrawn from or over-inserted into the tissue "T." In this manner, the surgical access assembly 1 is secured to the tissue "T" and longitudinal movement of the cannula 10 relative to the tissue "T" is prevented or minimized throughout insertion, withdrawal, and/or manipulation of a surgical instrument "S" through the cannula 10.

Following the surgical procedure, the expandable anchor 16 is deflated to permit the withdrawal of the cannula 10 from the tissue "T." The retention anchor 20 may remain secured to and disposed about the elongated shaft 12 of the cannula 10 in the second configuration during withdrawal of the cannula 10, or may be moved to the first configuration prior to removal of the cannula 10 from the tissue "T" (e.g., by applying a force against the second surface 26 of the annular body 22 towards the first surface 24 to pop the washer 34 back into the first configuration).

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical access assembly comprising:
a cannula including an elongated shaft; and
a retention anchor disposed about the elongated shaft and selectively slidable along the elongated shaft, the retention anchor including:
an annular body including an inner side surface defining an opening through the annular body, the annular body including a proximally-facing surface defining an annular recess in the proximally-facing surface; and a washer secured to the annular body, the washer including an inner terminal edge defining an opening through the washer that is aligned with the opening of the annular body, the elongated shaft of the cannula extending through the openings of the annular body and the washer, the washer transitionable between a first configuration in which the washer has a convex shape and the inner terminal edge of the washer is disposed outside of the annular recess so that the retention anchor is slidable along the elongated shaft, and a second configuration in which the washer has a concave shape and the inner terminal edge of the washer is disposed within the annular recess and engages the elongated shaft to fix the retention anchor to the elongated shaft.

2. The surgical access assembly of claim 1, wherein the inner side surface of the annular body frictionally engages the elongated shaft of the cannula.

3. The surgical access assembly of claim 2, wherein the inner side surface of the annular body includes ridges.

4. The surgical access assembly of claim 1, wherein the washer includes an outer terminal edge affixed to the annular body.

5. The surgical access assembly of claim 4, wherein the outer terminal edge of the washer is affixed to the annular body radially outwardly of the annular recess.

6. The surgical access assembly of claim 1, wherein, when the washer is in the first configuration, the washer extends proximally above the annular recess and, when the washer is in the second configuration, the washer is disposed within the annular recess.

7. The surgical access assembly of claim 1, wherein the washer is more rigid than the annular body.

8. The surgical access assembly of claim 7, wherein the washer is formed from a metal and the annular body is formed from a rubber.

9. The surgical access assembly of claim 1, wherein the washer is a continuous annular disk.

10. The surgical access assembly of claim 1, wherein, when the washer is in the first configuration, the entirety of the inner terminal edge of the washer is disposed outside of the annular recess.

11. A retention anchor for a surgical access device, the retention anchor comprising:
an annular body including an inner side surface defining an opening through the annular body, the annular body including a proximally-facing surface defining an annular recess in the proximally-facing surface; and
a washer secured to the annular body, the washer including an inner terminal edge defining an opening through the washer that is aligned with the opening of the annular body,
the washer transitionable between a first configuration in which the washer has a convex shape and the inner terminal edge of the washer is disposed outside of the annular recess, and a second configuration in which the washer has a concave shape and the inner terminal edge of the washer is disposed within the annular recess.

12. The retention anchor of claim 11, wherein the inner side surface of the annular body includes ridges.

13. The retention anchor of claim 11, wherein the washer includes an outer terminal edge affixed to the annular body.

14. The retention anchor of claim 11, wherein, when the washer is in the first configuration, the washer extends proximally above the annular recess and, when the washer is in second configuration, the washer is disposed within the annular recess.

15. The retention anchor of claim 11, wherein the washer is more rigid than the annular body.

16. The retention anchor of claim 15, wherein the washer is formed from a metal and the annular body is formed from a rubber.

17. The retention anchor of claim 11, wherein the washer is a continuous annular disk.

18. A method of securing a surgical access device to tissue, comprising:
positioning an elongated shaft of a cannula within tissue;
sliding a retention anchor disposed on the elongated shaft of the cannula distally until the retention anchor abuts an outer surface of the tissue, the retention anchor including:
an annular body having an inner surface defining an opening through the annular body, the annular body having a proximally-facing surface defining an annular recess in the proximally-facing surface; and
a washer secured to the annular body, the washer having an inner terminal edge defining an opening through the washer that is aligned with the opening of the annular body,
the elongated shaft of the cannula extending through the openings of the annular body and the washer, the washer disposed in a first configuration in which the washer has a convex shape and the inner terminal edge of the washer is disposed outside of the annular recess so that the retention anchor is slidable along the elongated shaft; and
moving the washer of the retention anchor to a second configuration in which the washer has a concave shape and the inner terminal edge of the washer is disposed within the annular recess and engages the elongated shaft to fix the retention anchor to the elongated shaft.

19. The method of claim 18, wherein moving the washer includes pressing the washer into the annular recess defined in the annular body of the retention anchor.

20. The method of claim 18, further including expanding an expandable anchor of the cannula against an inner surface of the tissue.

* * * * *